United States Patent [19]
Johnson

[11] Patent Number: 4,779,616
[45] Date of Patent: Oct. 25, 1988

[54] SURGICAL SUTURE-SNAGGING METHOD

[76] Inventor: Lanny L. Johnson, 3800 S. Hagadorn Rd., Okemos, Mich. 48864

[21] Appl. No.: 75,212

[22] Filed: Jul. 20, 1987

Related U.S. Application Data

[63] Continuation of Ser. No. 825,875, Feb. 4, 1986, abandoned.

[51] Int. Cl.$^4$ .................. A61B 17/04; A61B 17/06; D05B 87/00
[52] U.S. Cl. .................. 128/334 R; 128/340; 223/99
[58] Field of Search .................. 128/334 R, 340, 328; 223/99

[56] References Cited

U.S. PATENT DOCUMENTS

| | | | |
|---|---|---|---|
| 424,518 | 4/1890 | Van Norman | 223/99 |
| 2,042,403 | 5/1936 | Hrivnak | 223/99 |
| 2,411,118 | 11/1946 | Schuster | 223/99 |
| 2,416,260 | 2/1947 | Karle | 223/99 |
| 3,119,392 | 1/1964 | Zeiss . | |
| 3,152,466 | 10/1964 | Williams . | |
| 3,404,707 | 10/1968 | Feld | 223/99 |
| 3,874,388 | 4/1975 | King et al. . | |
| 4,102,478 | 7/1978 | Samoilov | 223/99 |
| 4,315,509 | 2/1982 | Smit . | |
| 4,393,872 | 7/1983 | Reznik et al. . | |
| 4,519,643 | 5/1985 | Harris . | |

Primary Examiner—Richard C. Pinkham
Assistant Examiner—Gary Jackson
Attorney, Agent, or Firm—Cushman, Darby & Cushman

[57] ABSTRACT

A method is provided for snagging a surgical suture wherein a device is introduced to the interior of the patient's body through a cylindrical cannula. The device includes a resilient loop which collapses as it passes through the cannula. The loop is crimped at its end whereby when a length of suture material is passed through the loop and the device is withdrawn from the patient through the cannula, the suture is snagged within the crimped portion so that it does not escape the loop.

2 Claims, 1 Drawing Sheet

U.S. Patent
Oct. 25, 1988
4,779,616
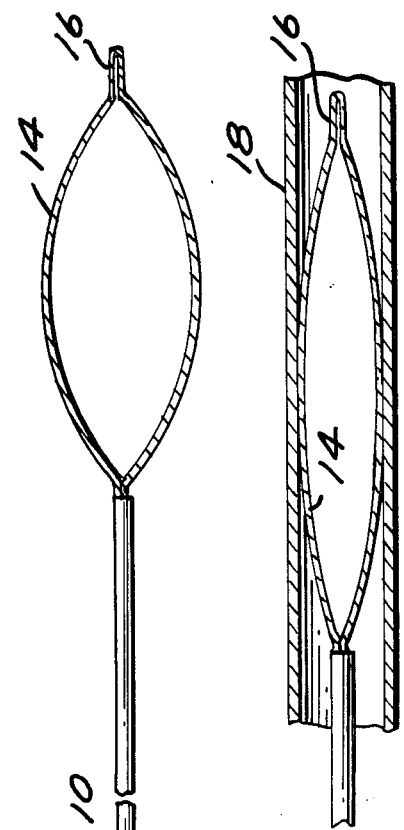
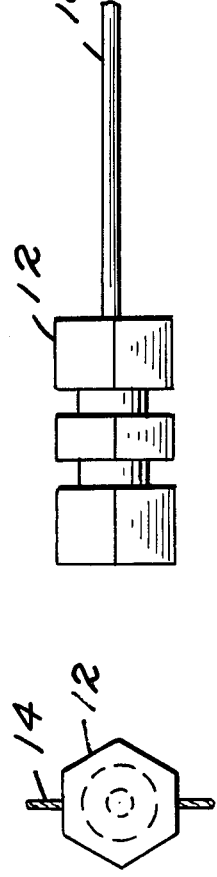
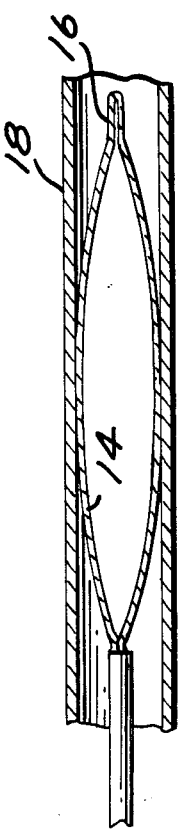
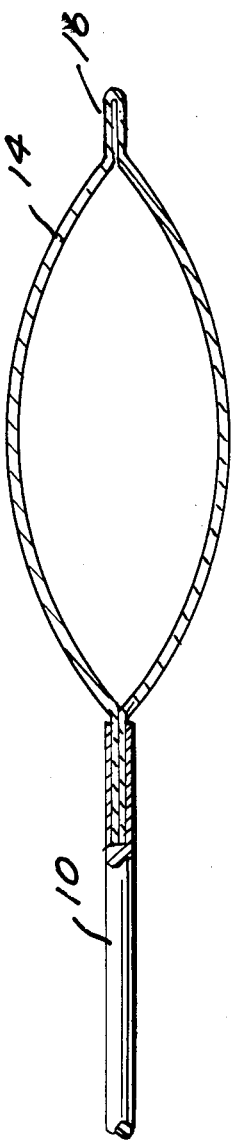

SURGICAL SUTURE-SNAGGING METHOD

This a continuation of application Ser. No. 825,875, filed Feb. 4, 1986, which was abandoned upon the filing hereof.

BACKGROUND OF THE INVENTION

Advancements in the science of arthroscopic surgery have resulted in a wide range of instruments being developed facilitating improved surgical techniques. However, because arthroscopy provides only limited direct access to the portion of the anatomy being operated on, problems unique to this type surgery persist. One such problem is the manipulation of lengths of suture material.

In conventional practice, one end of a strand of suture material is threaded onto a needle which is carried by a barrel-like device provided with a plunger. The needle-carrying end of the device is inserted through an opening in the patient's body to a position proximate the tissue which is to be sutured. The plunger then is actuated to force the needle outwardly from the body. As the needle emerges through the skin, it is grasped by the surgeon and is completely withdrawn so as to render accessible the said one end of the suture material. When the procedure is repeated with the other end of the material, both ends become exposed. The paths of needle travel in the procedural steps just described are generally parallel to one another in closely spaced relationship. Consequently, when the tissue spanning the separated portions of the suture material is cut, the surgeon can knot the ends drawing the knot tightly onto the tissue to complete the suture.

The method of suturing just described has several shortcomings, a principal one being the difficulty in accurately controlling the path of needle movement when the plunger is actuated. This lack of control can result in the needle causing neurovascular damage. Additionally, when the incision is made in the tissue spanning the separated portions of the suture material, the suture itself can be severed, thereby requiring the removal of its pieces and the substitution of another strand of material.

SUMMARY OF THE INVENTION

The shortcomings just described are overcome by the present invention. More particularly, a cylindrical cannula is deployed in an opening in the patient, and the distal end of the cannula is accurately positioned adjacent the tissue to be sutured. A collapsible loop secured to the end of an elongated handle is moved through the cannula from outside the body. As the loop emerges from the distal end of the cannula, the loop expands from its collapsed condition within the cannula. An end of suture material inserted through another opening in the patient's body is fed through the expanded loop. As the loop is withdrawn through the cannula, it snags the suture material and carries it outside the body. Using a second cannula and repeating the procedure, the other end of the suture material is rendered accessible to the surgeon who then can make an incision in the tissue spanning the two cannulas so that the suture can be completed when the cannulas are removed.

DETAILED DESCRIPTION OF THE INVENTION

The invention will be described in greater detail with respect to the accompanying drawings wherein:

FIG. 1 is a side elevational view of a suture-snagging surgical device capable of carrying out the method of the present invention;

FIG. 2 is an end elevational view thereof;

FIG. 3 is an enlarged side elevational view, partially in section, of a portion of the device shown in FIG. 1; and FIG. 4 is a sectional view of a portion of the device shown in FIG. 1 in operative relationship with a segment of a cylindrical needle.

Referring to FIGS. 1–3, an elongated rod 10 has secured to one end thereof a handle 12 of any convenient configuration. Preferably, rod 10 and handle 12 are formed of stainles steel. An elongated elliptically-shaped loop 14 is secured to the end of rod 10 opposite handle 12. Loop 14 preferably is formed of stranded stainless steel, and at its free end, the loop has a crimped portion 16. As can be appreciated from FIG. 3, the loop 14 is secured to rod 10 by its inner end being received and swaged within a cavity at the end of the rod.

Since loop 14 is formed of thin stranded lengths of wire, it is resilient whereby it can be compressed and then can return to its original configuration when the compression forces are released.

In FIG. 4, the loop 14 is illustrated in its compressed state within an elongated cylindrical cannula 18. A cannula suitable for use with loop 14 is a conventional spinal needle.

The structure having the capability of carrying out the present invention having been detailed, the manner in which it is employed now will be described.

In a typical arthroscopic procedure, three incisions are made to receive, respectively: an optic system (arthroscope) for allowing the involved surgical area to be viewed on a television monitor; the instruments for performing the surgery; and an irrigation device. When the surgical procedure requires suturing to facilitate the healing process—as, for example, in mending menisci—it is necessary to introduce suture material to the area of the tissue involved. In accordance with the present invention, a pair of cannulas 18 are inserted through the skin in closely spaced relationship. Since the distal ends of the cannulas can be carefully and accurately directed to positions adjacent the suturing location, the opportunity for unnecessary neurovascular damage is reduced. The surgeon then grasps the surgical device by handle 12 and passes loop 14 through one of the cannulas 18. During its passage, the loop is compressed (FIG. 4), but as it leaves the distal end of the cannula, loop 14 expands to the shape shown in FIGS. 1 and 3. The surgeon then inserts one end of a length of suture material through the incision provided for receiving the surgical instruments. Utilizing the television monitor for guidance, the end of the suture material is threaded through loop 14. The loop then is withdrawn through cannula 18. As the loop re-enters the distal end of the cannula, the suture material is snagged within the crimped portion 16 of the loop. This prevents the material from escaping the loop. When the loop completely exits the proximal end of cannula, the captured end of the suture material is removed from the loop. The surgeon then inserts the device through the second cannula 18, whereupon the procedure just described is repeated for the other end of the length of suture material.

Both ends of the suture material now being accessible to the surgeon, an incision is made between the two cannulas. The suture material is protected by the cannulas when this occurs. The cannulas then are removed, the suture material is knotted about the tissue being repaired, and the loose ends are trimmed to complete the suturing procedure.

What is claimed is:

1. A method for snagging an end of a surgical suture located within a patient's body during arthroscopic surgery, comprising the steps of:

deploying a distal end of a cylindrical cannula adjacent the end of said suture within said body;

passing a resilient loop through the cannula from a proximal end thereof towards said distal end of said cannula into said body, said loop being secured to a distal end of an elongated rod and having a portion which is crimped at a location opposite to where the loop is secured to the rod;

inserting the suture end through said loop as the loop extends beyond the distal end of the cannula within said body; and withdrawing the rod and the loop from the cannula whereby the end of the suture is snagged in the crimped portion of the loop and then is displaced so as to emerge from the proximal end of the cannula.

2. A method as set forth in claim 1, wherein said loop is substantially elliptical in shape, the width of the loop being greater than the inner diameter of the cannula whereby the loop is compressed when it passes through the cannula.

* * * * *